(12) United States Patent
Vuong (10) Patent No.: US 11,147,712 B2
(45) Date of Patent: Oct. 19, 2021

(54) OCULAR SHIELD FOR FACILITATING GENERATION OF VISUAL EVOKED POTENTIALS (VEP)

(71) Applicant: Shawn Michael Vuong, Sioux Falls, SD (US)

(72) Inventor: Shawn Michael Vuong, Sioux Falls, SD (US)

(*) Notice: Subject to any disclaimer, the term of this patent is extended or adjusted under 35 U.S.C. 154(b) by 226 days.

(21) Appl. No.: 16/273,220

(22) Filed: Feb. 12, 2019

(65) Prior Publication Data

US 2020/0078219 A1 Mar. 12, 2020

Related U.S. Application Data

(60) Provisional application No. 62/728,817, filed on Sep. 9, 2018.

(51) Int. Cl.
*A61N 5/06* (2006.01)
*A61F 9/06* (2006.01)
*A61B 5/378* (2021.01)
*A61B 5/16* (2006.01)

(52) U.S. Cl.
CPC ............. *A61F 9/06* (2013.01); *A61B 5/378* (2021.01); *A61N 5/0613* (2013.01); *A61B 5/16* (2013.01); *A61B 2562/0247* (2013.01); *A61N 2005/0648* (2013.01)

(58) Field of Classification Search
CPC .......... A61N 2005/0648; A61N 5/0613; A61B 5/163; A61B 5/378; A61B 5/6821
See application file for complete search history.

(56) References Cited

U.S. PATENT DOCUMENTS

| 2,379,629 | A | * | 7/1945 | Eweson | A61F 9/0061 294/1.2 |
|---|---|---|---|---|---|
| 5,456,508 | A | * | 10/1995 | Kozar | A61F 9/0061 294/1.2 |
| 6,820,979 | B1 | | 11/2004 | Stark | |
| 8,764,185 | B1 | * | 7/2014 | Biederman | G02C 7/04 351/159.02 |
| 2012/0245444 | A1 | * | 9/2012 | Otis | H01L 31/0682 600/345 |
| 2013/0211389 | A1 | * | 8/2013 | Chuck | A61B 18/20 606/5 |

(Continued)

OTHER PUBLICATIONS

Eveline M. Gutwillerr,Intraoperative monitoring with visual evoked potentials for brain surgeries, JNS.

*Primary Examiner* — Tajash D Patel (57) ABSTRACT

An ocular shield for facilitating generation of Visual Evoked Potentials (VEP) is disclosed. The ocular shield may include a body configured to be disposed over an ocular globe of an eye. Further, the body may include an interior surface and an exterior surface. Further, the ocular shield may include at least one light source configured to generate at least one light emission. Further, the at least one light source may be coupled to the body to facilitate transmission of the at least light emission from the interior surface of the body. Further, the ocular shield may include a power source, electrically coupled to the at least one light source, configured to provide electrical energy to the at least one light source. Further, the ocular shield may include a controller configured to control the power source. Further, the controller may be electrically coupled to the power source.

18 Claims, 8 Drawing Sheets

(56) References Cited

U.S. PATENT DOCUMENTS

| | | | |
|---|---|---|---|
| 2014/0005514 A1* | 1/2014 | Pugh | A61N 1/0468 |
| | | | 600/383 |
| 2014/0277291 A1* | 9/2014 | Pugh | G02C 7/04 |
| | | | 607/88 |
| 2017/0086670 A1 | 3/2017 | Lowrance | |
| 2018/0161203 A1* | 6/2018 | Hopper | A61B 90/30 |
| 2018/0264284 A1* | 9/2018 | Alvarez | A61N 5/0618 |
| 2020/0268321 A1* | 8/2020 | Lemole, Jr. | A61B 5/4047 |

* cited by examiner

OCULAR SHIELD FOR FACILITATING GENERATION OF VISUAL EVOKED POTENTIALS (VEP)

RELATED APPLICATION(S)

Under provisions of 35 U.S.C. § 119e, the Applicant(s) claim the benefit of U.S. provisional application No. 62/728,817 filed Sep. 9, 2018, which is incorporated herein by reference.

FIELD OF THE INVENTION

The present invention relates generally to electronic devices. More specifically, the present invention is an apparatus and method to facilitate controlling of an ocular shield including a controllable light source.

BACKGROUND OF THE INVENTION

Currently, visual evoked potentials (VEP) are difficult to obtain consistently in surgical procedures. Further, goggles are currently used to hold mechanisms and devices to elicit visual evoked potentials during surgeries, However, goggles may move during surgical approaches due to movement of the scalp of a patient. Further, goggles may not protect eyes perfectly during surgical procedures. Further, apparatuses, which may offer protection to eyes, and ocular globes of patients, while housing mechanisms to elicit visual evoked potentials during the surgical procedures do not exist.

Therefore, there is a need for improved ocular shields for facilitating generating of visual evoked potentials that may overcome one or more of the above-mentioned problems and/or limitations.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, an ocular shield for facilitating generation of Visual Evoked Potentials (VEP) is disclosed. The ocular shield may include a body configured to be disposed over an ocular globe of an eye. Further, the body may include an interior surface and an exterior surface.

Further, the ocular shield may include at least one light source configured to generate at least one light emission. Further, the at least one light source may be coupled to the body to facilitate transmission of the at least light emission from the interior surface of the body.

Further, the ocular shield may include a power source, electrically coupled to the at least one light source, configured to provide electrical energy to the at least one light source.

Further, the ocular shield may include a controller configured to control the power source. Further, the controller may be electrically coupled to the power source.

Further, an ocular shield for facilitating generation of Visual Evoked Potentials (VEP) is disclosed. The ocular shield may include a body configured to be disposed over an ocular globe of an eye. Further, the body may include an interior surface and an exterior surface.

Further, the ocular shield may include at least one light source configured to generate at least one light emission. Further, the at least one light source may be coupled to the body to facilitate transmission of the at least light emission from the interior surface of the body Further, the ocular shield may include at least one interconnect configured to electrically connect the at least one light source to an external device.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of an ocular shield including a controllable light source, embodiments of the present disclosure are not limited to use only in this context.

Figure 1:
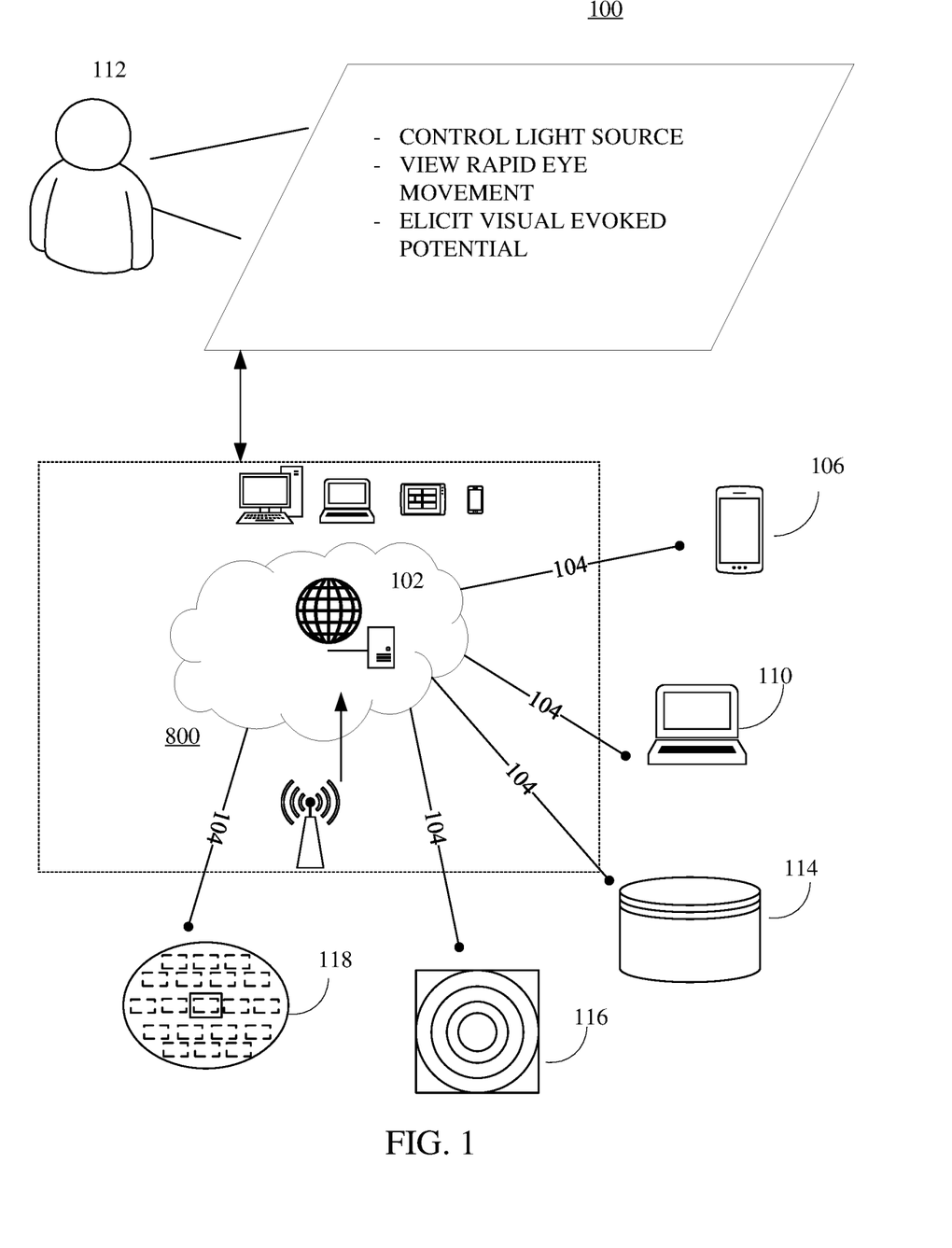
FIG. 1 is an illustration of an online platform consistent with various embodiments of the present disclosure.

FIG. 1 is an illustration of an online platform 100 consistent with various embodiments of the present disclosure. By way of non-limiting example, the online platform 100 to facilitate controlling of an ocular shield including a controllable light source may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, sensors 116, actuators (not shown) and an ocular shield 118 over a communication network 104, such as, but not limited to, the Internet. Further, users of the online platform 100 may include relevant parties such as, but not limited to, neurologists, ophthalmologists, intra-operative neuromonitoring technicians, patients and end users. Accordingly, in some instances, electronic devices operated by the one or more relevant parties may be in communication with the platform.

Figure 8:
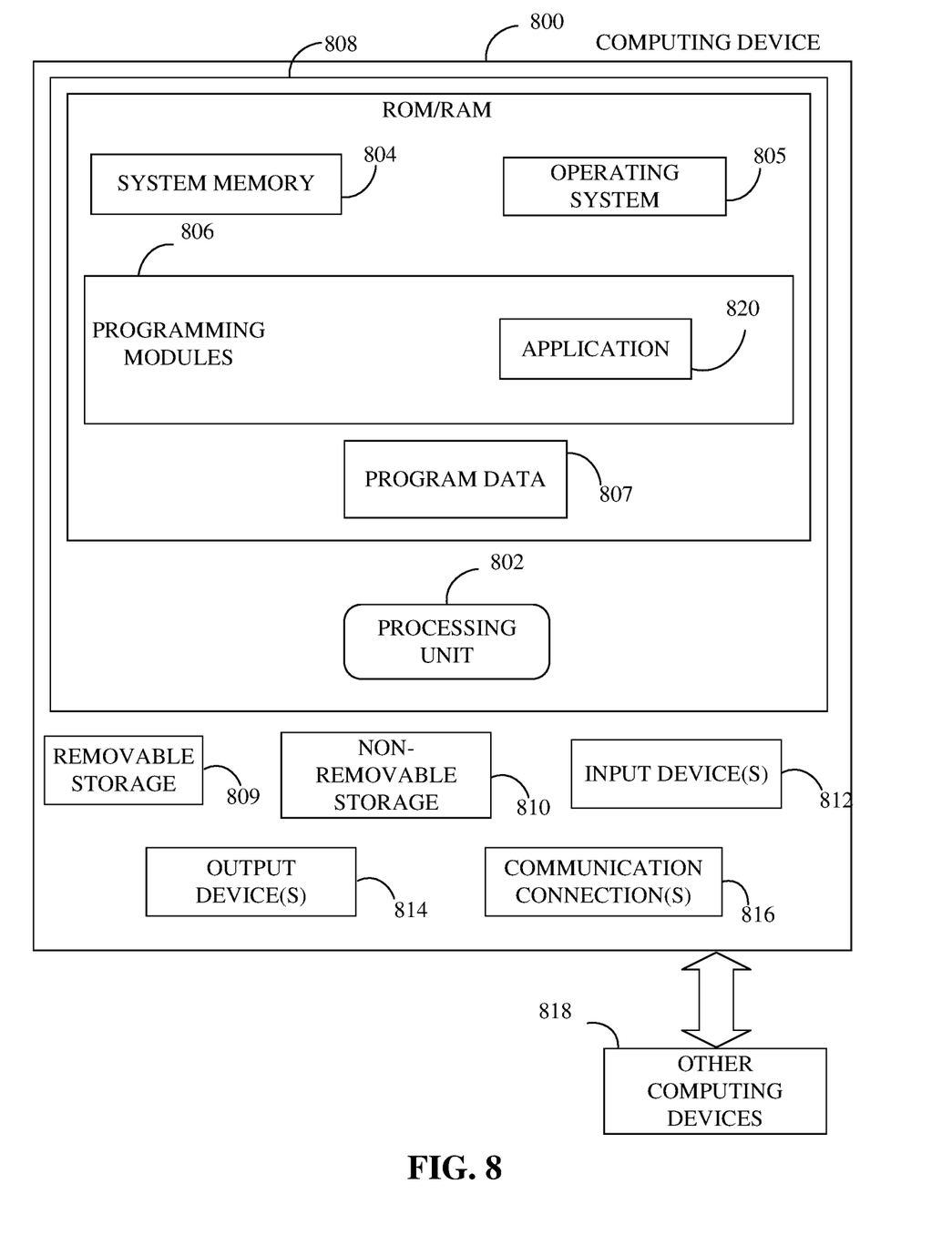
FIG. 8 is a block diagram of a computing device for implementing the methods disclosed herein, in accordance with some embodiments.

A user 112, such as the one or more relevant parties, may access online platform 100 through a web based software application or browser. The web based software application may be embodied as, for example, but not be limited to, a website, a web application, a desktop application, and a mobile application compatible with a computing device 800.

According to some embodiments, the online platform 100 may be configured to facilitate controlling of an ocular shield including a controllable light source. The ocular shield may be shaped to be placed over the ocular globe of an eye. Further, the ocular shield may include a light source, such as LEDs disposed on the interior face. The light source may be configured to emit light for a continued time, or in small flashes in one or more pre-defined and preset patterns. The emission of light through the light source in the preset and pre-defined patterns may elicit a visual evoked potential in an occipital cortex of the patient to detect continued visual function, such as during neurosurgery.

Further, the online platform 100 may be used to control the light source in the ocular shield. For instance, the ocular shield may interface with the online platform 100 over a communication network, such as a mobile network, Wi-Fi, Bluetooth, and so on, and may allow control of one or more functions and operations of the ocular shield to one or more authorized devices, such as smartphones, laptop computers, desktop computers, and so on corresponding to one or more operators of the ocular shield, including doctors, and other medical personnel.

Further, the online platform 100 may store one or more operational profiles associated with the ocular device, which may define one or more operational parameters associated with an ocular shield. For instance, an operational profile associated with an ocular shield may include a number of emissions of light by powering a light source ON and OFF (number of flashes), the frequency of the flashes, such as frequency in a minute, or second, and an intensity of the flashes, such as brightness of light of the light source, and whether the brightness of different flashes is same or different, and so on.

Figure 2:
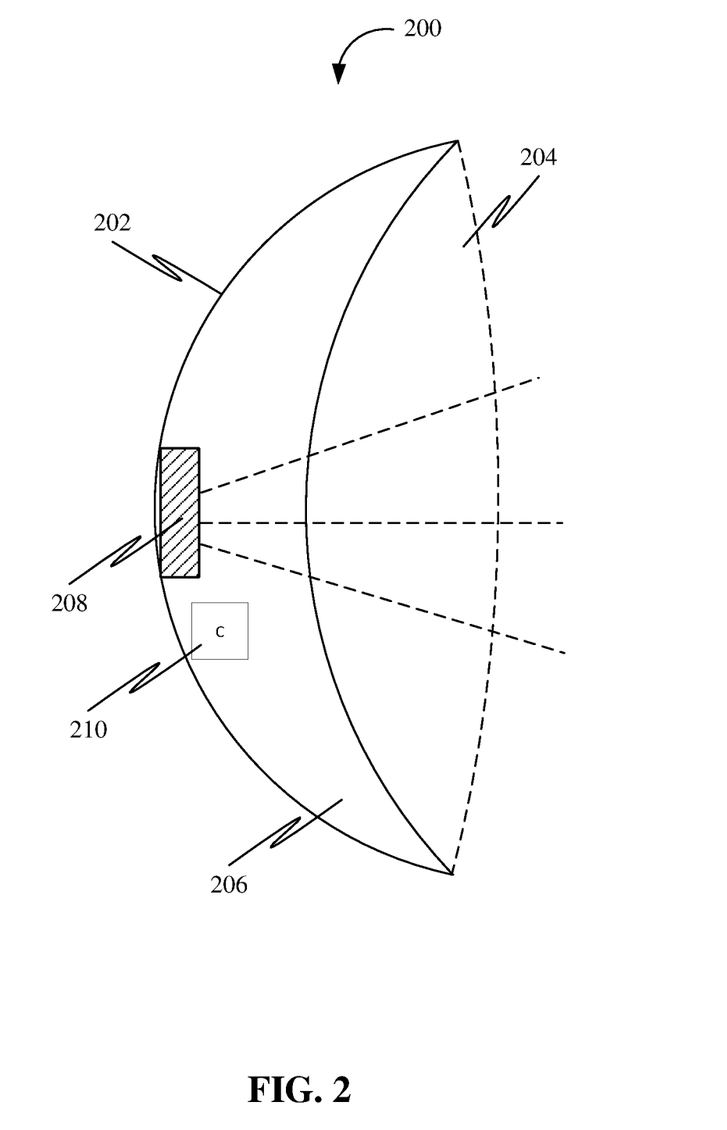
FIG. 2 shows an ocular shield for facilitating generation of Visual Evoked Potentials (VEP), in accordance with some embodiments.

FIG. 2 shows an ocular shield 200 for facilitating generation of Visual Evoked Potentials (VEP) is disclosed. The ocular shield 200 may include a body 202 configured to be disposed over an ocular globe of an eye. Further, the body 202 may include an interior surface 204 and an exterior surface 206. Further, a shape of the interior surface 204 may be configured to conform to at least a part of the ocular globe. For example, the part of the ocular globe may include the cornea.

Further, in an embodiment, the ocular shield 200 may be shaped in a manner to be placed comfortably over the eye. For instance, the ocular shield 200 may be shaped in a symmetrically or asymmetrically spherical, elliptical, bi-elliptical, multi-elliptical or toroidal manner.

Further, the ocular shield 200 may cover the cornea and the sclera of the ocular globe. Further, in an embodiment, the body 202 of the ocular shield 200 may include a support extension. Further, the support extension may comprise a significantly flattened edge comprising an outer boundary of the ocular shield 200. Further, the ocular shield 200 may be placed over the ocular globe in a manner such that the eyelids may cover a part of the support extension. Accordingly, the covering of the part of the support extension may provide additional stability to the ocular globe, and may not allow the ocular globe to fall off when placed over the ocular globe.

Further, in an embodiment, the ocular shield 200 may be shaped to ensure a sufficient gap between the ocular shield 200 and the ocular globe. Further, the interior surface 204 of the ocular shield 200 may be sufficiently congruent to a surface of the ocular globe.

Further, the ocular shield 200 may be fabricated from hard materials such as acrylics like polymethylmethacrylate, or metals such as stainless steel, from plastics, or from flexible materials such as silicone.

Further, the ocular shield 200 may be manufactured using conventional manufacturing processes. For instance, the ocular shield 200 may be manufactured using laser machining, turning, swaging, casting (semi mound or full mound), injection molding or any combinations thereof.

Further, the size of the ocular shield 200 may vary. The ocular shield 200 may be fabricated in multiple sizes so as to be comfortably placed over ocular globes of multiple sizes corresponding to multiple patients. For instance, the ocular shield 200 may be fabricated in diameters of roughly 19 mm, 21 mm, 23 mm, and 25 mm to be comfortably placed over ocular globes of sizes corresponding to the diameters of the ocular shield 200s.

Further, in an embodiment, the ocular shield 200 may be manufactured according to a topography of the ocular globe of an individual. For instance, geometric values related to the topography, including a shape of the eye, circumference, and diameter of the cornea, an area of the sclera, and so on may be obtained with the aid of three-dimensional measuring methods. Further, ocular biometry may be performed to measure the shape and size of the eye using optical coherence interferometry, ultrasound technology, and so on. Subsequently, a 3D printer may be used to produce the ocular shield 200 of the required geometrical measurements. Further, an embodiment, a turning process may be employed to produce the ocular shield 200 from a blank of required materials with cutting tools.

Further, the ocular shield 200 may include at least one light source configured to generate at least one light emission. Further, the at least one light source may be coupled to the body 202 to facilitate transmission of the at least light emission from the interior surface 204 of the body 202.

Further, the at least one light source 208 may be configured to emit light for a continued time, or in small flashes in one or more pre-defined and preset patterns. The emission of light through the at least one light source, in the preset and pre-defined patterns may elicit the visual evoked potential in an occipital cortex of the patient to detect continued visual function, such as during neurosurgery.

Further, in an embodiment, the at least one light source may include a single point light source, such as an LED configured to emit the at least light emission from the interior surface 204 of the body 202. Further, the at least one light emission may include at least one light pulse emitted from the single point light source. Further, the at least one light pulse may correspond to one or more of a duration, and a brightness. Further, if the at least one light emission includes a plurality of the at least one light pulse, the plurality of the at least one light pulse may correspond to one or more of a duration, a brightness, an intermittent time, and a number of the plurality of light pulse.

Further, in an embodiment, the at least one light source may include a plurality of point light sources, such as LEDs configured to emit the at least light emission from the interior surface 204 of the body 202. Further, the plurality of point light sources may be disposed on the interior surface 204. Further, the plurality of point light sources may be equidistant. Further, in an embodiment, the plurality of point light sources may be disposed on the interior surface 204 of the body 202 to form a pattern, such as a geometric shape (for e.g. a square, a circle, a triangle, a spiral, and so on). Further, the plurality of point light sources may be configured to emit the at least light emission so as to elicit a pattern to evoke VEP.

Further, in an embodiment, the at least one light source may include a flexible display device, such as an LCD, an LED display, an AMOLED display, and so on disposed on the interior surface 204 of the body 202. Further, the flexible display device may be configured to emit the at least light emission from the interior surface 204 of the body 202. Further, the at least light emission emitted from the flexible display device may include a flash, a pattern, an image, and so on to evoke VEP. Further, the at least one light emission emitted from the flexible display device may be monochromatic, or polychromatic.

Further, the ocular shield 200 may include a power source configured to provide electrical energy to the at least one light source. Further, the power source may be electrically coupled to the at least one light source.

In some embodiments, a wired connection may emerge out of the outer surface of the ocular shield 200 and may be connected to the power source of the ocular shield 200. Accordingly, the power source may comprise an external power source, such as a battery, an AC mains outlet from grid, and so on configured to transmit electrical energy over the wired connection.

In some embodiments, the power source may include a printable battery printed on a surface, such as the outer surface of the ocular shield 200. Accordingly, the power source may be configured to provide electrical energy to the at least one light source through an electrical interconnect.

Further, in some embodiments, the power source may include an RFID receiver configured to receive targeted radio waves. Further, the RFID receiver may be configured to be energized through the targeted radio waves, and provide electrical energy to the at least one light source.

Further, the ocular shield 200 may include a controller 210 configured to control the power source. Further, the controller 210 may be electrically coupled to the power source.

In some embodiments, the ocular shield 200 may further include an input device configured to receive at least one control data. Further, the controller 210 may be configured to control the power source based on the at least one control data. Further, the input device may be configured to receive the at least one control data from at least one external device. Further, the at least one external device may include a user device, such as a smartphone, a laptop computer, a desktop computer, and so on.

In some embodiments, the at least one control data may include at least one emission characteristic corresponding to the at least one light source.

Further, in some embodiments, the at least one emission characteristic may relate to a type of the at least one light emission. For instance, the type of the at least one light emission may include a flash or a pattern. For instance, the pattern may include a monochrome checkboard pattern.

Further, the at least one emission characteristic may control the at least one light emission, including the type of the at least one light emission to control type of VEP that may be generated. For instance, if the at least one light source is configured to emit a monochrome checkboard pattern, including a fixation dot, the at least one emission characteristic may include a size of each check in the monochrome checkboard pattern. Further, the at least one emission characteristic may include a size of a visual field. For instance, the at least one emission characteristic may define a visual field subtending 10-40 degrees of arc and an individual check size of about 1 degree of arc. The check size may allow generating VEP in patients lacking good visual acuity. Further, the at least one emission characteristic may affect a recorded VEP. For instance, VEP with a large amplitude and fastest peak may be recorded using a smallest possible check size that the patient may be able to view see sharply. For instance, a patient with 20/20 (6/6) or better vision may produce a largest amplitude, and fastest VEP components using a small check size (a visual field comprised of checks only 5-6 mm, perceived at 1 meter). Each check may measure about 15-20' of arc. further, a patient with poor visual acuity may produce the largest amplitude, fastest VEP components with a larger check size subtending 1 degree or more (such as a 20 mm check or larger projected at a distance of 1 meter.

In some embodiments, the at least one emission characteristic may include one or more of an intensity, a spectral bandwidth range, a polarization value, a start time, an end time, a time period, a frequency of pulsations, a duty cycle, a temporal pattern, and a spatial pattern.

For instance, the at least one emission characteristic may control a simulation rate (frequency of pulsation) of the at least one light source to control a type of VEP. For instance, the at least one emission characteristic may control a simulation rate of the at least one light source to 3 or more pulsations per second to generate a steady state VEP. Further, the at least one emission characteristic may control a simulation rate of the at least one light source to less than 3 pulsations per second to generate a transient VEP. Further, the at least one emission characteristic may include appearing or disappearing a pattern, such as the monochrome checkerboard pattern to generate onset, and offset VEPs respectively.

In some embodiments, the ocular shield 200 may further include a storage device configured for storing the at least one control data.

In some embodiments, the ocular shield 200 may further include a wireless receiver configured to receive the control data from a computing device.

In some embodiments, the ocular shield 200 may further include at least one electrical interconnect configured to electrically couple the at least one light source to the controller 210. Accordingly, in some embodiments, the ocular shield 200 may be operable by connecting with a computing device such as a laptop computer, a smartphone etc. through an interconnect such as, but not limited to, USB interface. Further, each of the power source and the controller 210 may be comprised in a computing device.

The controller 210 may allow control of the at least one light source, such as through control of electrical power to the at least one light source, and control of the at least one emission characteristic, and the one or more patterns of light emitted by the at least one light source to elicit visual evoked potential in the patient.

In some embodiments, the power source may be controllable through a wireless transceiver connected to the controller 210. Further, the power source may be connected to a switch to control operation of the power source. Further, the switch may be controllable through the wireless transceiver connected to the controller 210. Accordingly, in place of the interconnect, such as a USB interface, the wireless transceiver may be used to control the operation of the light source in the ocular shield 200. Further, the wireless transceiver may interface with a comparing device, such as a smartphone, desktop computer, a tablet computer, and so on over a communication network, such as a mobile communication network, infrared, radio, Bluetooth, Wi-Fi, and so on, and may allow control of the operation of the at least one light source. Further, in an embodiment, the at least one light source may be powered through resonant inductive coupling, wherein the operation of the power source may be controlled through the wireless transceiver over a communication network, such as a mobile communication network, infrared, radio, Bluetooth, Wi-Fi, and so on.

In some embodiments, the ocular shield 200 may further include a gripper connectable to the exterior surface 206. Further, the gripper may be configured to facilitate application, positioning, and removal of the ocular shield 200.

In some embodiments, the gripper may include a stud formed on the exterior surface 206. Further, the gripper may be configured to be manipulated with human fingers.

In some embodiments, the gripper may be configured to be detachably connected to the exterior surface 206.

In some embodiments, the gripper may include a suction cup. In an embodiment, the gripper may be a small stud or peg-like structure formed on the exterior surface 206 of the ocular shield 200, which may be gripped and may allow the manipulation of the ocular shield 200. Further, the gripper may include a handle like structure formed on the exterior surface 206 of the ocular shield 200. Further, the gripper may be permanently attached to the ocular shield 200. Further, in an embodiment, the gripper may be detachable and may be detached upon the placement of the ocular shield 200 over the ocular globe. For instance, the ocular shield 200 may include at least one receiving groove on the external face, into which the gripper may be inserted and attached. Further, in an embodiment, the gripper may be separate from the ocular shield 200 and may be used only for the placement, and the removal of the ocular shield 200 over, and from the ocular globe. For instance, the gripper may include a cylindrical peg including a suction cup at one end. The suction cup may connect to the ocular shield 200 and may aid in gripping the ocular shield 200, and further manipulation as required, such as application, removal, and adjustment.

In some embodiments, the interior surface 204 may include a light reflective coating configured to reflect the at least one light emission. Further, the light reflective coating may be configured to reflect the at least one light emission from the at least one light source towards the cornea. Further, in an embodiment, the light reflective coating may include aluminum coating, a gold coating, silver coating, and so on. Further, the light reflective coating may include a dielectric coating, which may be manufactured using materials with a different refractive index to the body 202, such as magnesium fluoride, calcium fluoride, and various metal oxides.

In some embodiments, the exterior surface 206 may include an optical barrier configured to prevent light transmission from the exterior side to the interior surface 204. For instance, the ocular shield 200 may be constructed of an opaque material to prevent light transmission from the exterior side to the interior surface 204 and to prevent exposure of the cornea to external light sources while the ocular shield 200 may be placed over the ocular globe.

In some embodiments, the ocular shield 200 may further include a transmitter configured to transmit the at least one control data to a VEP monitoring device. Further, the VEP monitoring device may be configured for capturing at least one VEP in response to the at least one light emission. Further, the VEP may be configured to store the at least one control data in association with the at least one VEP.

In some embodiments, the at least one light source may include a plurality of light sources spatially distributed over a planar region of the body 202. Further, the body 202 may include a camera disposed at a predetermined position on the planar region. Further, the camera may be configured to capture an image of at least a part of the ocular globe. Further, the camera may be configured to be communicatively coupled to the controller 210. Further, the controller 210 may be configured for determining a position of a pupil of the ocular globe in relation to the planar region. Further, the controller 210 may be configured for identifying a light source based on the determining. Further, a position of the light source on the planar region may be vertically aligned with a center of the pupil.

Further, in an embodiment, the ocular shield 200 may include a plurality of the at least one light source at multiple locations on the interior face. For instance, the multiple locations of the plurality of the at least one light source may correspond to multiple locations of the pupil of the patient after the patient has been anesthetized, such as for surgery. Further, the plurality of the at least one light source in the ocular shield 200 may be illuminated all at once in accordance with input received from the controller 210 to elicit visual evoked potential regardless of the position of the pupil. Further, in an embodiment, the position of the pupil may be determined by an additional sensor in the ocular shield 200, such as a camera. Further, in an embodiment, the ocular shield 200 may include a processor to determine the position of the pupil from input images captured by the camera. Further, the processor may control the plurality of the at least one light source at the multiple locations corresponding to the position of the pupil as determined from the input captured by the camera.

Further, in an embodiment, the position of the pupil may rapidly change, such as during Rapid Eye Movement (REM). Further, the position of the pupil may be determined through the input captured by the camera. Further, in an embodiment, the ocular shield 200 may include a plurality of the at least one light source along the entire surface area of the interior surface 204. Accordingly, to simulate the pupil during REM, and elicit visual evoked potential, the input captured by the camera may be analyzed by the processor and may be used to actuate the plurality of the at least one light source corresponding to the position of the pupil during REM.

In some embodiments, the interior surface 204 may be configured to adhere to at least the part of the ocular globe. Further, subsequent to placement of the ocular shield 200 over the part of the ocular globe, the ocular shield 200 may remain stationary in relation to the ocular globe in spite of a movement of the ocular globe.

In some embodiments, the body 202 may comprise of a biocompatible material. Further, the biocompatible material may not produce a toxic or immunological response when exposed to a body of the patient, or bodily fluids thereof. Further, the body 202 may comprise a metallic biocompatible material such as titanium, or a ceramic biocompatible material such as Alumina (Al2O3), Zirconia (ZrO2), Bioglass (Na2OCaOP2O3-SiO), and so on. Further, the body 202 may comprise a biocompatible material composed of synthetic polymers such as water-repelling materials like α-hydroxyacid, polyanhydrides, and so on. Further, the body 202 may comprise biocompatible materials including natural polymers such as Polyvinylchloride (PVC), Polyethylene (PE), Polypropylene (PP), Polymethylmetacrylate (PMMA), Polystyrene (PS), Polytetrafluoroethylene (PTFE), Polyurethane (PU), Polyethylenterephthalate (PET), and so on.

In some embodiments, the body 202 may be sterile. Further, in an embodiment, the ocular shield 200 may be constructed using a material safe enough to be used in an autoclave for the purpose of sterilization.

Figure 3:
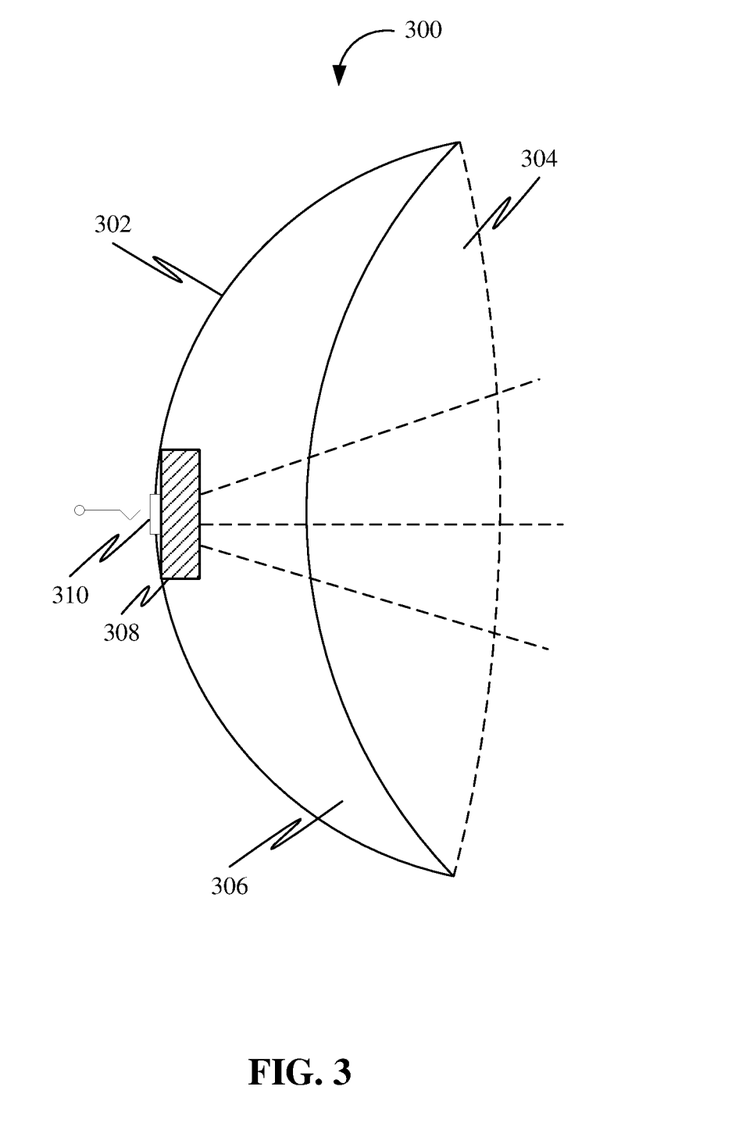
FIG. 3 shows an ocular shield for facilitating generation of Visual Evoked Potentials (VEP), including an electrical interconnect, in accordance with some embodiments.

FIG. 3 shows an ocular shield 300 for facilitating generation of Visual Evoked Potentials (VEP), including an electrical interconnect, in accordance with some embodiments. The ocular shield 300 may include a body 302 configured to be disposed over an ocular globe of an eye. Further, the body 302 may include an interior surface 304 and an exterior surface 306. Further, a shape of the interior surface 304 may be configured to conform to at least a part of the ocular globe Further, the ocular shield 300 may include at least one light source 308 configured to generate at least one light emission. Further, the at least one light source 308 may be coupled to the body to facilitate transmission of the at least light emission from the interior surface 304 of the body 302.

Further, the ocular shield 300 may include at least one interconnect 310 configured to electrically connect the at least one light source 308 to an external device.

Further, the at least one interconnect 310 may include a power source configured to provide electrical energy to the at least one light source 308. Further, the power source may be electrically coupled to the at least one light source 308 through the at least one interconnect 310.

Further, the at least one interconnect 310 may include a controller configured to control the power source. Further, the controller may be electrically coupled to the power source.

Figure 4:
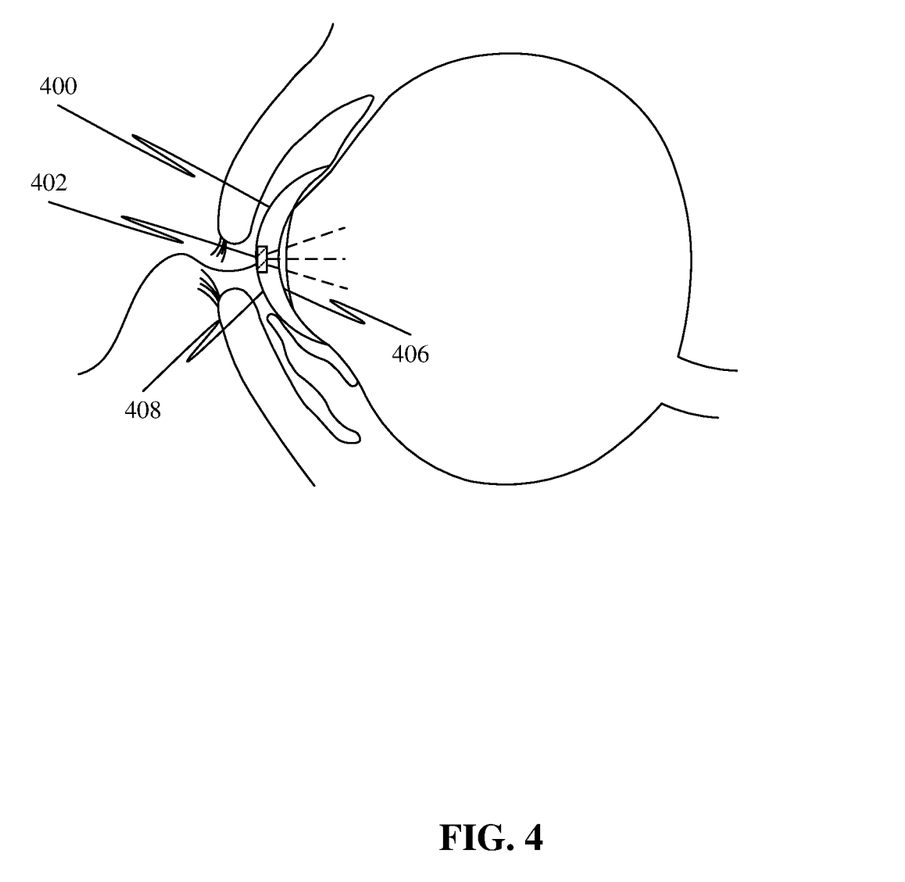
FIG. 4 shows an exemplary ocular shield including a light source to elicit visual evoked potential, in accordance with some embodiments.

FIG. 4 shows an exemplary ocular shield 400. The ocular shield 400 may be shaped to be placed over the ocular globe of an eye. As such, the ocular shield 400 may be circular shaped. Alternatively, the shape of the ocular shield 400 may be mostly round, oval, or elliptical. The shape of the ocular shield 400 may aid in comprehensive and complete coverage of the ocular globe. Further, the ocular shield 400 may include an interior face 404, corresponding to a side of the ocular shield 400 that may face the ocular globe of the eye. The interior face 404 of the ocular shield 400 may be somewhat concave, and the may conform to the convex shape of the cornea. Further, a sufficient gap may be present between the cornea, and the interior face 404 of the ocular shield 400, so that the inner face may not interface with, and intrude upon the cornea and leading to a potential flattening and irritation of the cornea. Furthermore, the ocular shield 400 may include an exterior face 408 408, which may face away from the ocular globe of the eye. Further, the exterior face 408 may be somewhat convex in accordance with the concave shape of the interior face 404.

Further, the ocular shield 400 may include an upper edge and a lower edge. The length of the upper edge of the ocular shield 400 may be more than the length of the lower edge. Further, the ocular shield 400 may include notches alongside the length the upper edge and the lower edge of the ocular shield 400. The notch may interface with the eyelids and may aid in maintaining a snug fit of the ocular shield 400 over the ocular globe. The notch may be machined on the ocular shield 400 by flattening a sufficient length of the edge of the ocular shield 400. Further, the inner face, outer face, the edges, and the notch together may constitute a main body of the ocular shield 400. Further, the entire surface of the ocular shield 400 may be smooth and polished. The smooth surface may lead to protection from irritation arising from abrasion of the ocular globe against the rough surface, edges, or notches of the ocular shield 400.

Figure 5:
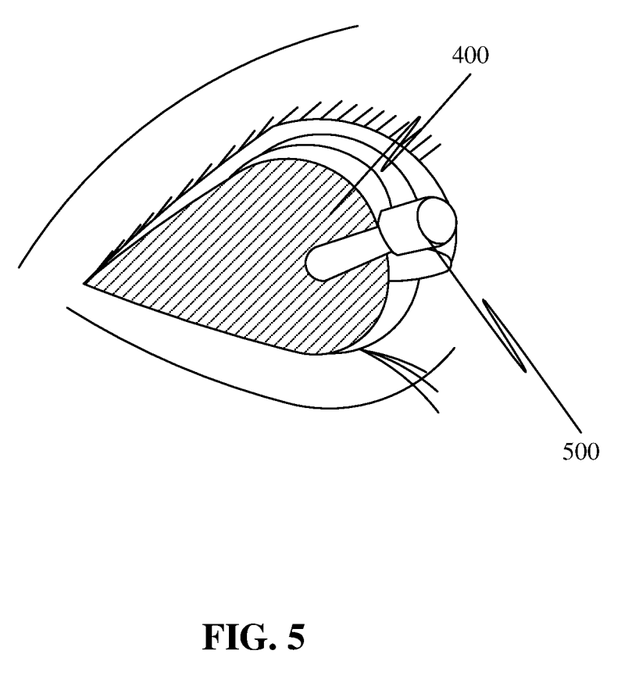
FIG. 5 shows a stud or peg-like gripping mechanism of the ocular shield of FIG. 4.
Figure 6:
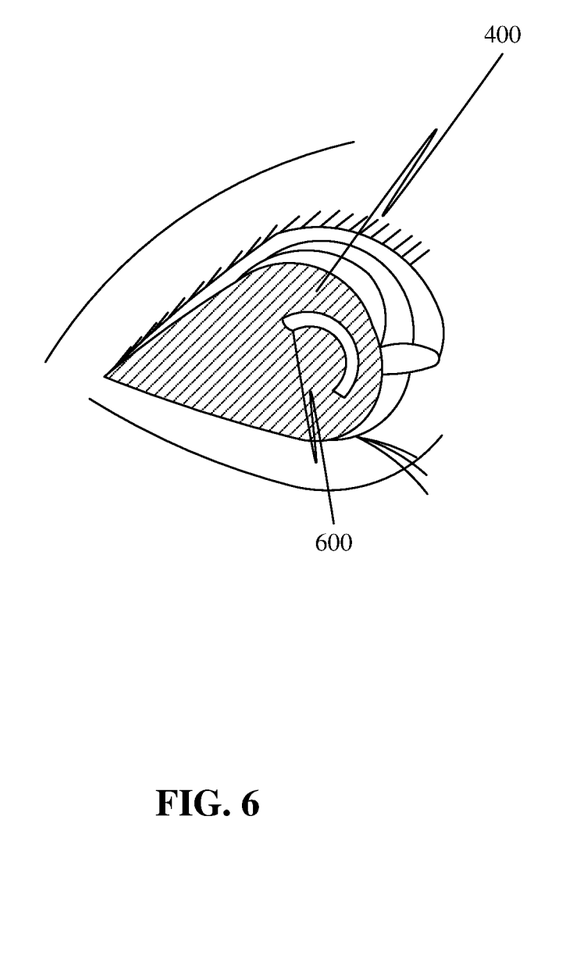
FIG. 6 shows a handle like gripping mechanism of the ocular shield of FIG. 4.

Further, a gripping mechanism may be connected to the ocular shield 400 to allow easy application, positioning, and removal of the ocular shield 400. In an instance, the gripping mechanism may be a small stud or peg-like structure formed on the outer face of the ocular shield 400, which may be gripped and may allow the manipulation of the ocular shield 400. Further, the gripping mechanism may include a stud or peg like gripping mechanism 50 structure as shown in FIG. 5. Further, the gripping mechanism may include a handle like gripping mechanism 600 structure as shown in FIG. 6. Further, the gripping mechanism may be of a material similar, or different from a material of the main body of the ocular shield 400. Further, the gripping mechanism may be permanently attached to the ocular shield 400. Further, in an embodiment, the gripping mechanism may be detachable and may be detached upon the placement of the ocular shield 400 over the ocular globe. For instance, the ocular shield 400 may include a one or more receiving groove on the external face, into which the detachable gripping members may be inserted and attached. Further, in an embodiment, the gripping mechanism may be separate from the ocular shield 400 and may be used only for the placement, and the removal of the ocular shield 400 over, and from the ocular globe. For instance, the gripping mechanism may include a cylindrical peg including a suction cup at one end. The suction cup may connect to the ocular shield 400 and may aid in gripping the ocular shield 400, and further manipulation as required, such as application, removal, and adjustment.

Further, the ocular shield 400 may be made of an opaque material so as to prevent exposure of the cornea to external light sources while the shield may be placed over the ocular globe. Further, the ocular shield 400 may be fabricated from hard materials such as acrylics like polymethylmethacrylate, or metals such as stainless steel, from plastics, or from flexible materials such as silicone. Further, the ocular shield 400 may be used in an autoclave for the purpose of sterilization.

Further, the size of the ocular shield 400 may vary. The ocular shield 400 may be fabricated in multiple sizes so as to be comfortably placed over ocular globes of multiple sizes corresponding to multiple patients. For instance, the ocular shield 400 may be fabricated in diameters of roughly 19 mm, 21 mm, 23 mm, and 25 mm to be comfortably placed over ocular globes of sizes corresponding to the diameters of the ocular shield 400s.

Further, the ocular shield 400 may include at least one light source 402, such as at least one LED disposed on the interior face 404. The at least one light source 402 may be configured to emit light for a continued time, or in small flashes in one or more pre-defined and preset patterns. The emission of light through the at least one light source 402 in the preset and pre-defined patterns may elicit a visual evoked potential in an occipital cortex of the patient to detect continued visual function, such as during neurosurgery.

Figure 7:
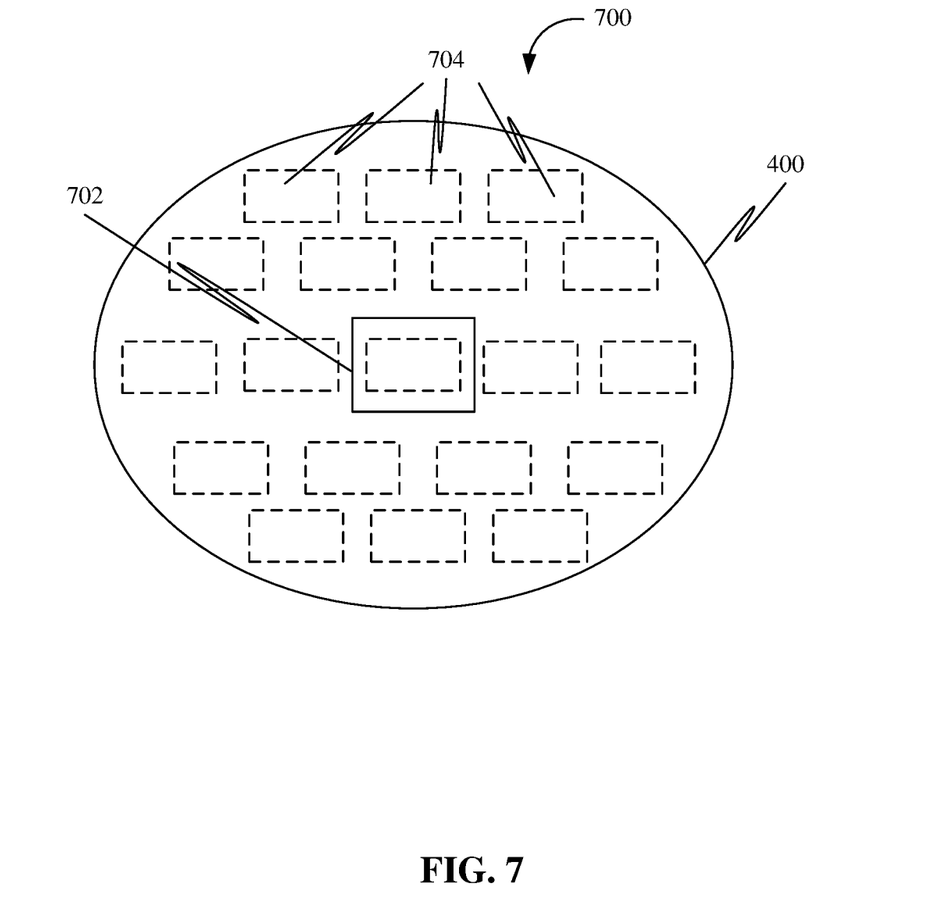
FIG. 7 shows a block diagram of the ocular shield, in accordance with some embodiments

Further, the at least one light source 402 may be connected to a controller 702, such as through a small cord, as shown in a block diagram 700 in FIG. 7. The controller 702 may allow control of the light source, such as control of the power to the light source, and control of one or more patterns of light emitted by the at least one light source 402 to elicit visual evoked potential in the patient.

Further, in an embodiment, the at least one light source 402 may be coupled to a power source and a switch, which may be controllable through a wireless transceiver included in the controller 702. Accordingly, in place of a wired connection emerging out of the ocular shield 400, the wireless transceiver may be used to control the operation of the at least one light source 402 in the ocular shield 400. Further, the wireless transceiver, may interface with an external device, such as a smartphone, desktop computer, a tablet computer, and so on over a communication network, such as a mobile communication network, infrared, radio, Bluetooth, Wi-Fi, and so on, and may allow control of the operation of the light source. Further, in an embodiment, the at least one light source 402 in the ocular shield 400 may be powered through resonant inductive coupling, wherein the operation of the power source may be controlled through the wireless transceiver over a communication network, such as a mobile communication network, infrared, radio, Bluetooth, Wi-Fi, and so on.

Further, in an embodiment, the in addition to power, the intensity of the at least one light source 402 may also be wirelessly controllable. Accordingly, the number of emissions of light by powering the at least one light source 402 ON and OFF (flashes), the frequency of the flashes, such as frequency in a minute, or second, and an intensity of the flashes, such as brightness of light of the light source, and whether the brightness of different flashes is same or different may be wirelessly controllable.

Further, in an embodiment, the at least one light source 402 may be a simple point at least one light source 402 and may be configured to generate one or more beams of concentrated light, such as in a laser. Further, the intensity of one or more generated light beams may be low so as not to damage the ocular globe, cornea, or the pupil of the patient. Alternatively, the simple point at least one light source 402 may be configured to emit diffused light.

Further, the at least one light source 402 may include an array of lights. The array may include a plurality of lights laid out in one or more patterns. Further, the array of lights may be configured to be illuminated in specific order to elicit visual evoked potential in the patient.

Further, in an embodiment, the at least one light source 402 of the ocular shield 400 may include a plurality of light sources 704 704 at multiple locations on the interior face 404. For instance, the multiple locations of the plurality of light sources 704 may correspond to multiple locations of the pupil of the patient after the patient has been anesthetized, such as for surgery. Further, the plurality of light sources 704 in the ocular shield 400 may be illuminated all at once in accordance with input received from the controller 702 to elicit visual evoked potential regardless of the position of the pupil. Further, in an embodiment, the position of the pupil may be determined by an additional sensor in the ocular shield 400, such as a camera. Further, the ocular shield 400 may include a processor to determine the position of the pupil from input images captured by the camera. Further, the processor may control the light sources at the multiple locations corresponding to the position of the pupil as determined from the input captured by the camera.

Further, in an embodiment, the position of the pupil may rapidly change, such as during Rapid Eye Movement (REM). Further, the position of the pupil may be determined through the input captured by the camera. Further, the ocular shield 400 may include a plurality of light sources 704 along the entire surface area of the interior face 404. Accordingly, to simulate the pupil during REM, and elicit visual evoked potential, the input captured by the camera may be analyzed by the processor and may be used to actuate the plurality of light sources 704 corresponding to the position of the pupil during REM.

Further, in an embodiment, the ocular shield 400 may be used in acute traumatic brain injury (TBI) to follow reactivity of the pupil after flashes of light with camera. If the pupil is slower to react, the slower reaction of the pupil may represent increased brain injury or hemorrhage.

Further, in an embodiment, the ocular shield 400 may include a storage device (memory) connected to the light source. Further, the storage device may store one or more stimulation commands related to the at least one light source 402 as received from the controller 702. For instance, stimulation commands generating a particular sequence of operation of the light source, frequency of flashes of light from the light source, such as frequency in a minute, or second, and an intensity of the flashes, such as brightness of light of the light source, and whether the brightness of different flashes is same or different may be saved.

Further, in an embodiment, the ocular shield 400 may include an additional sensor, so as to detect one or more properties related to the eye of the patient during surgery, or during assessment of acute traumatic injury, such as acute traumatic injury sustained due to a motor vehicle collision. For instance, the ocular shield 400 may include a pressure sensor, which may be in contact with the ocular globe of the patient. Further, the pressure sensor may be used to measure pressure on the ocular globe of the patient during surgery. Accordingly, the pressure sensor may be used to measure external pressure on the ocular globe, and the eye of the patient. Further, the pressure sensor may also transmit an alert, such as to one or more connected devices and/or monitors if the pressure on the ocular globe and the eye of the patient increases beyond a preset threshold value.

Further, in an embodiment, the additional sensor may operate in conjunction with the light source. For instance, the at least one light source 402 may be activated to elicit a visual evoked potential. Further, the additional sensor, such as the pressure sensor may continually monitor external pressure on the eye and the ocular globe during surgery. Accordingly, the data recorded from the visual evoked potential, and the pressure sensor may be correlated to determine and assess visual function.

Further, in an embodiment, the visual function of the patient, as determined using the visual evoked potential using the at least one light source 402 and/or the additional sensor may be correlated to additional parameters, such as length of the surgery, and physiological data of the patient such as EKG, pulse oximetry, arterial pressure, and so on, which may be simultaneously measured using one or more appropriate monitors.

With reference to FIG. 8, a system consistent with an embodiment of the disclosure may include a computing device or cloud service, such as computing device 800. In a basic configuration, computing device 800 may include at least one processing unit 802 and a system memory 804. Depending on the configuration and type of computing device, system memory 804 may comprise, but is not limited to, volatile (e.g. random-access memory (RAM)), non-volatile (e.g. read-only memory (ROM)), flash memory, or any combination. System memory 804 may include operating system 805, one or more programming modules 806, and may include a program data 807. Operating system 805, for example, may be suitable for controlling computing device 800's operation. In one embodiment, programming modules 806 may include image-processing module, machine learning module and/or image classifying module. Furthermore, embodiments of the disclosure may be practiced in conjunction with a graphics library, other operating systems, or any other application program and is not limited to any particular application or system. This basic configuration is illustrated in FIG. 8 by those components within a dashed line 808.

Computing device 800 may have additional features or functionality. For example, computing device 800 may also include additional data storage devices (removable and/or non-removable) such as, for example, magnetic disks, optical disks, or tape. Such additional storage is illustrated in FIG. 8 by a removable storage 809 and a non-removable storage 810. Computer storage media may include volatile and nonvolatile, removable and non-removable media implemented in any method or technology for storage of information, such as computer-readable instructions, data structures, program modules, or other data. System memory 804, removable storage 809, and non-removable storage 810 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 800. Any such computer storage media may be part of device 800. Computing device 800 may also have input device(s) 812 such as a keyboard, a mouse, a pen, a sound input device, a touch input device, a location sensor, a camera, a biometric sensor, etc. Output device(s) 814 such as a display, speakers, a printer, etc. may also be included. The aforementioned devices are examples and others may be used.

Computing device 800 may also contain a communication connection 816 that may allow device 800 to communicate with other computing devices 818, such as over a network in a distributed computing environment, for example, an intranet or the Internet. Communication connection 816 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 804, including operating system 805. While executing on processing unit 802, programming modules 806 (e.g., application 820 such as a media player) may perform processes including, for example, one or more stages of methods, algorithms, systems, applications, servers, databases as described above. The aforementioned process is an example, and processing unit 802 may perform other processes. Other programming modules that may be used in accordance with embodiments of the present disclosure may include machine learning application etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the invention has been explained in relation to its preferred embodiment, it is to be understood that many other possible modifications and variations can be made without departing from the spirit and scope of the invention.

What is claimed is:

1. An ocular shield for facilitating generation of Visual Evoked Potentials (VEP), the ocular shield comprising:
   a body configured to be disposed over an ocular globe of an eye, wherein the body comprises an interior surface and an exterior surface, wherein a shape of the interior surface is configured to conform at least a part of the ocular globe;
   at least one light source configured to generate at least one light emission, wherein the at least one light source is coupled to the body to facilitate transmission of the at least light emission from the interior surface of the body;

a power source configured to provide electrical energy to the at least one light source, wherein the power source is electrically coupled to the at least one light source;

a controller configured to control the power source, wherein the controller is electrically coupled to the power source;

wherein the at least one light source comprises a plurality of light sources spatially distributed over a planar region of the body, wherein the body further comprises a camera disposed at a predetermined position on the planar region, wherein the camera is configured to capture an image of at least a part of the ocular globe, wherein the camera is configured to be communicatively coupled to the controller, wherein the controller is configured for:

determining a position of a pupil of the ocular globe in relation to the planar region; and identifying the plurality of light sources based on the determining, wherein a position of the plurality of light sources on the planar region is vertically aligned with a center of the pupil.

2. The ocular shield of claim 1 further comprising an input device configured to receive at least one control data, wherein the controller is configured to control the power source based on the at least one control data.

3. The ocular shield of claim 2, wherein the at least one control data comprises at least one emission characteristic corresponding to the at least one light source.

4. The ocular shield of claim 3, wherein the at least one emission characteristic comprises at least one of an intensity, a spectral bandwidth range, a polarization value, a start time, an end time, a time period, a frequency of pulsations, a duty cycle, a temporal pattern and a spatial patters.

5. The ocular shield of claim 2 further comprising a storage device configured for storing the at least one control data.

6. The ocular shield of claim 5 further comprising a wireless receiver configured to receive the control data from a computing device.

7. The ocular shield of claim 1 further comprising at least one electrical interconnect configured to electrically couple the at least one light source to the controller, wherein each of the power source and the controller is comprised in a computing device.

8. The ocular shield of claim 1, wherein the at least one light source comprises at least one light emitting diode (LED).

9. The ocular shield of claim 1 further comprising a gripper connectable to the exterior surface, wherein the gripper is configured to facilitate application, positioning, and removal of the ocular shield.

10. The ocular shield of claim 9, wherein the gripper comprises a stud formed on the exterior surface, wherein the gripper is configured to be manipulated with human fingers.

11. The ocular shield of claim 9, wherein the gripper is configured to be detachably connected to the exterior surface.

12. The ocular shield of claim 11, wherein the gripper comprises a suction cup.

13. The ocular shield of claim 1, wherein the interior surface comprises a tight reflective coating configured to reflect the at least one light emission.

14. The ocular shield of claim 1, wherein the exterior surface comprises an optical barrier configured to prevent light transmission from the exterior side to the interior surface.

15. The ocular shield of claim 2 further comprising a transmitter configured to transmit the at least one control data to a VET monitoring device, wherein the VEP monitoring device is configured for capturing at least one VEP in response to the at least one light emission, wherein the VEP is further configured to store the at least one control data in association with the at least one VEP.

16. The ocular shield of claim 1, wherein the interior surface is configured to adhere to at least the part of the ocular globe, wherein subsequent to placement of the ocular shield over the part of the ocular globe, the ocular shield remains stationary in relation to the ocular globe in spite of a movement of the ocular globe.

17. The ocular shield of claim 1, wherein the body comprises of a biocompatible material.

18. The ocular shield of claim 1, wherein the body is sterile.

* * * * *